(12) United States Patent
Bousquet

(10) Patent No.: US 10,676,760 B2
(45) Date of Patent: Jun. 9, 2020

(54) METHOD FOR PRODUCING ETHANOL AND ETHANOL PRODUCING SYSTEM

(71) Applicant: Valmet AB, Sundsvall (SE)

(72) Inventor: Jean-Pierre Bousquet, Norcross, GA (US)

(73) Assignee: Valmet AB (SE)

( * ) Notice: Subject to any disclaimer, the term of this patent is extended or adjusted under 35 U.S.C. 154(b) by 545 days.

(21) Appl. No.: 15/334,430

(22) Filed: Oct. 26, 2016

(65) Prior Publication Data

US 2018/0112237 A1    Apr. 26, 2018

(51) Int. Cl.
| | |
|---|---|
| *C12P 7/10* | (2006.01) |
| *C12P 7/06* | (2006.01) |
| *C10L 1/00* | (2006.01) |
| *C10L 1/02* | (2006.01) |

(52) U.S. Cl.
CPC .............. *C12P 7/06* (2013.01); *C10L 1/00* (2013.01); *C10L 1/023* (2013.01); *C12P 7/10* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 9,243,364 B2 * | 1/2016 | Zhu | C12P 7/10 |
| 9,249,432 B2 * | 2/2016 | Brunecky | C12P 7/14 |
| 9,328,393 B2 * | 5/2016 | Medoff | C08H 8/00 |
| 9,873,846 B2 * | 1/2018 | Hill | C05D 9/00 |
| 2009/0029432 A1 | 1/2009 | Abbas et al. | |
| 2012/0040423 A1 * | 2/2012 | Grundberg | C12P 7/10 |
| | | | 435/145 |
| 2015/0105593 A1 | 4/2015 | Radtke et al. | |

FOREIGN PATENT DOCUMENTS

WO    2011111692 A1    9/2011

OTHER PUBLICATIONS

Modenbach, A. et al., Biomass and Bioenergy 2013 vol. 56 pp. 526-544.*
Ozer, A. et al J. Chem.Technol. Biotechnol. 2000 vol. 75 pp. 1061-1065.*
Aditiya H.B. et al., "Second generation bioethanol production: A critical review" Renewable and Sustainable Energy Reviews, 2016, 66, 631-653; whole document.
Cheng et al., "High titer and yield ethanol production from undetoxified whole slurry of Douglas-fir forest residue using pH profiling in SPORL" Biotechnology for Biofuels (2015), 8:22, 1-10; p. 5, right hand column.
International Search Report including the Written Opinion for Application No. PCT/SE2017/051021 dated Nov. 15, 2017.
Muktham R. et al., "A Review on 1st and 2nd Generation Bioethanol Production-Recent Progress" Journal of Sustainable Bioenergy Systems, 2016, 6, 72-92; whole document.

* cited by examiner

*Primary Examiner* — Heidi Reese
(74) *Attorney, Agent, or Firm* — Lerner, David, Littenberg, Krumholz & Mentlik, LLP

(57) ABSTRACT

The invention relates to a method for producing ethanol comprising providing biomass, supplying yeast to the biomass, reducing the size of the biomass, fermentation of the biomass at a solid content of above 20%, and distilling the fermented biomass. It also relates to an ethanol producing system comprising biomass providing arrangement, a yeast supplying device for supplying yeast to the biomass, a biomass size reducing device configured to reduce the size of the biomass, a fermentation device configured to ferment the biomass at a solid content of above 20% and a distilling device.

23 Claims, 5 Drawing Sheets

METHOD FOR PRODUCING ETHANOL AND ETHANOL PRODUCING SYSTEM

FIELD OF THE INVENTION

The present invention relates to a method for producing ethanol and an ethanol producing system.

BACKGROUND OF THE INVENTION

In ethanol production biomass, such as sugar cane, energy cane and sorghum, is used as raw material. A typical ethanol production process is shown below. Biomass stalks are shredded or cut to reduce the size of the biomass material. Then the biomass stalks are pressed and the resulting stalk juice is filtrated and concentrated by evaporation. The free sugar molecules in the sugar solution, resulting from the filtration, are fermented and the fermented solution is distilled to purify and concentrate the ethanol. Thereafter the ethanol is dehydrated. The ethanol production process is shown in FIG. 5.

The ethanol production process shown in FIG. 5 has several drawbacks. It comprises several steps and is thus complicated. It requires a large amount of water, chemicals and energy and is thus expensive and not environmentally friendly.

As a consequence, in light of the above drawbacks, there is a need of an improved method for producing ethanol and an improved ethanol producing system which are less complicated, less expensive and more environmentally friendly.

SUMMARY OF THE INVENTION

An object of the present invention is to provide an improved method and system for producing ethanol which may at least partly improve on the drawbacks of the prior art mentioned above.

These and other objects are achieved by a method for producing ethanol and an ethanol producing system according to the independent claims.

According to a first aspect of the invention, a method for producing ethanol is provided. The method comprises providing biomass, supplying yeast to the biomass, reducing the size of the biomass, optionally adding water to the biomass such that the solid content of the biomass is above 20%, fermentation of the biomass with a solid content of above 20%, and distilling the fermented biomass. Thereby, it is possible to provide a method for producing ethanol which comprises fewer steps and thereby is less complicated and less expensive. Due to the high solid content, i.e. low water content, little or no evaporation is necessary before fermentation.

In other words, the method comprises adding no water or only a limited amount of water prior to fermentation, the quantity of water being added being adjusted such that the solid content is above 20%. The step of optionally adding water may alternatively be described as a step of controlling the water content of the biomass such that it has a solid content of above 20%. In an embodiment of the first aspect of the invention, the solid content is above 50%, or above 80%.

In an embodiment of the first aspect of the invention, no water is added before the step of fermentation of the biomass, i.e. the step of optionally adding water is omitted. Thereby no evaporation is required and it is possible to provide a method for producing ethanol which requires less energy, is more environmentally friendly and less expensive. Furthermore, the yield of ethanol per unit weight of total solids in the raw material may increase.

In an embodiment of the first aspect of the invention where water is added, the water may be added before the step of reducing the size or between the step of reducing the size and the step of fermentation of the biomass. In other embodiments, the water may be added together with the yeast, for example, the yeast may be in liquid form.

In an embodiment of the first aspect of the invention, reducing the size of the biomass comprises using an atmospheric refiner. Thereby it is possible to provide a method for producing ethanol which do not degrade the free sugar molecules. Further, using an atmospheric refiner increases the amount of insoluble solids, i.e. carbohydrates in insoluble form, which transition into dissolved solids (DS), i.e. carbohydrates in soluble form. Thus, the amount of DS is increased. DS is defined as the total solid content minus the insoluble solids. The carbohydrates in soluble form migrates to the liquid portion of the biomass. Thereby, the amount of carbohydrates available for processing into ethanol is increased. Consequently, the method produces an even higher yield of ethanol per unit weight of total solids in the raw material and the amount of residual bagasse is decreased.

In an embodiment of the first aspect of the invention, providing biomass comprises providing whole plants. It is understood that providing whole plants implies that all parts of the plant are used, but not necessarily that the plant is used in one piece, i.e. the plant may be cut into smaller pieces before the yeast is added and before the plant is further reduced in size. This embodiment is advantageously combined with the embodiment described below where the length of the biomass is reduced to a length less than about 100 mm during harvest. The use whole plants leaves less residual biomass in the harvested field. Thereby, the yield of ethanol per acre of cultivated field is increased and the disposal of residual solids is reduced.

In an embodiment of the first aspect of the invention, the step of supplying yeast to the biomass is performed before the step of reducing the size of the biomass. Thereby the mixing of the biomass and the added yeast is improved, and the yield is further improved.

In an embodiment of the first aspect of the invention, the method further comprises separating the fermented biomass into a liquid portion and a solid portion.

In an embodiment of the first aspect of the invention, the method further comprises heating the solid portion to produce ethanol vapour and distilling the ethanol vapour.

In an embodiment of the first aspect of the invention, the method further comprises separating the liquid portion, into a light phase and a dense phase, and distilling the light phase. Separating the liquid portion may comprise sedimentation of the liquid portion.

In an embodiment of the first aspect of the invention, the method further comprises separating the yeast from the dense phase. Separating the yeast may comprise centrifuging the dense phase.

In an embodiment of the first aspect of the invention, the method further comprises recycling the yeast by using the recovered yeast in the step comprising supplying yeast to the biomass. Thereby it is possible to provide a method for producing ethanol which is more environmentally friendly and less expensive.

In an embodiment of the first aspect of the invention, providing biomass comprises providing sugar cane and/or energy cane and/or sorghum. Sorghum doesn't require ideal growing conditions and is thus relatively inexpensive to grow. Thereby it is possible, if sorghum is used as raw material, to provide a method for producing ethanol which is less expensive.

In an embodiment of the first aspect of the invention, providing biomass comprises growing the biomass, harvesting the biomass and transporting the biomass. Harvesting the biomass may comprise reducing the length of the biomass to a length less than about 100 mm.

In an embodiment of the first aspect of the invention, reducing the size of the biomass comprises reducing the length of the biomass to a length in the range between about 1-2 mm. Thereby the surface area of the biomass is increased and thereby it is possible to provide a method for producing ethanol which produces a higher yield of ethanol per unit weight of total solids in the raw material.

In an embodiment of the first aspect of the invention, the fermentation comprises using a fermentation downward tower.

In an embodiment of the first aspect of the invention, separating the fermented biomass comprises using a screw press.

In an embodiment of the first aspect of the invention, heating the solid portion comprises using a horizontal screw reactor.

In an embodiment of the first aspect of the invention, distilling comprises using a distillation column.

In an embodiment of the first aspect of the invention, the method further comprises conveying the biomass using a screw conveyer and supplying yeast to the biomass comprises supplying yeast to the biomass in the screw conveyor. Thereby the mixing of the biomass and the added yeast is improved.

In an embodiment of the first aspect of the invention, cleaning the biomass is performed before the step of supplying yeast to the biomass. Thereby the quality of the raw material that will be further processed is improved and thereby the life time of the ethanol producing system is extended, as it reduces the damage related to abrasion due to the presence of, for example, sand and stones, particularly upon biomass having been mechanically harvested.

According to a second aspect of the invention an ethanol producing system for carrying out the method according to the first aspect of the invention is provided. The system comprises a biomass providing arrangement, a yeast supplying device for supplying yeast to the biomass, a biomass size reducing device configured to reduce the size of the biomass, a fermentation device configured to ferment the biomass at a solid content of above 20% and a distilling device. The system optionally comprises a water addition device. Thereby, it is possible to provide an ethanol producing system which is less complicated, do not require chemicals, is more environmentally friendly and less expensive.

In an embodiment of the second aspect of the invention, the biomass size reducing device comprises an atmospheric refiner. Thereby it is possible to provide an ethanol producing system which do not degrade the free sugar molecules. Further, the atmospheric refiner increases the amount of insoluble solids which transition into dissolved solids (DS). Thus, the amount of DS is increased. The carbohydrates in soluble form migrates to the liquid portion of the biomass. Thereby, the amount of carbohydrates available for processing into ethanol is increased. Consequently, the system produces a higher yield of ethanol per unit weight of total solids in the raw material and decreases the amount of residual bagasse.

In an embodiment of the second aspect of the invention, the yeast supplying device is arranged upstream the biomass size reducing device. Thereby, the biomass and the yeast are mixed in the biomass size reducing device and thereby the mixing of the biomass and the yeast is improved.

In an embodiment of the second aspect of the invention, the ethanol producing system further comprises first separating device for separating the fermented biomass into a liquid portion and a solid portion.

In an embodiment of the second aspect of the invention, the ethanol producing system further comprises heating device for heating the solid portion to produce ethanol vapour.

In an embodiment of the second aspect of the invention, the ethanol producing system further comprises second separating device for separating the liquid portion into a light phase and a dense phase.

In an embodiment of the second aspect of the invention, the second separation device comprises sedimentation device.

In an embodiment of the second aspect of the invention, the ethanol producing system further comprises third separation device for separating the yeast from the dense phase.

In an embodiment of the second aspect of the invention, the third separation device comprises a centrifuge.

In an embodiment of the second aspect of the invention, the ethanol producing system further comprises recycling device for recycling the recovered yeast to the yeast supplying device. Thereby it is possible to provide an ethanol producing system which is more environmentally friendly.

In an embodiment of the second aspect of the invention, the biomass providing device comprises growing device, harvesting device and transporting device. The harvesting device may be configured to reduce the length of the biomass to a length less than about 100 mm.

In an embodiment of the second aspect of the invention, the biomass size reducing device is configured to reduce the length of the biomass to a length in the range between about 1-2 mm. Thereby the surface area of the biomass material is increased and thereby it is possible to provide an ethanol producing system which produces a higher yield of ethanol per unit weight of total solids in the raw material.

In an embodiment of the second aspect of the invention, the fermentation device comprises a fermentation downward tower.

In an embodiment of the second aspect of the invention, the first separating device comprises a screw press.

In an embodiment of the second aspect of the invention, the heating device comprises a horizontal screw reactor.

In an embodiment of the second aspect of the invention, the distilling device comprises a distillation column.

In an embodiment of the second aspect of the invention, the ethanol producing system further comprises conveying device comprising a screw conveyor and the yeast supplying device is arranged upstream the screw conveyor. Thereby the biomass and the yeast is mixed in the screw conveyor and thereby the mixing of the biomass and the yeast is improved.

In an embodiment of the second aspect of the invention, the ethanol producing system comprises cleaning device for cleaning the biomass. Thereby the quality of the raw material that will be further processed is improved and thereby the life time of the ethanol producing system is extended, as it reduces the damage related to abrasion due to the presence of, for example, sand and stones, particularly upon biomass having been mechanically harvested.

In an embodiment of the second aspect of the invention, the biomass size reducing device is configured to reduce the size of the biomass such that the solid content of the biomass is above 50%.

In an embodiment of the second aspect of the invention, the biomass size reducing device is configured to reduce the size of the biomass such that the solid content of the biomass is above 80%.

Further embodiments and advantages of the present invention are evident from the following detailed description.

BRIEF DESCRIPTION OF THE DRAWINGS

In the following the invention is described with reference to embodiments of the present invention and the accompanying drawings, in which.

DETAILED DESCRIPTION

Figure 1:
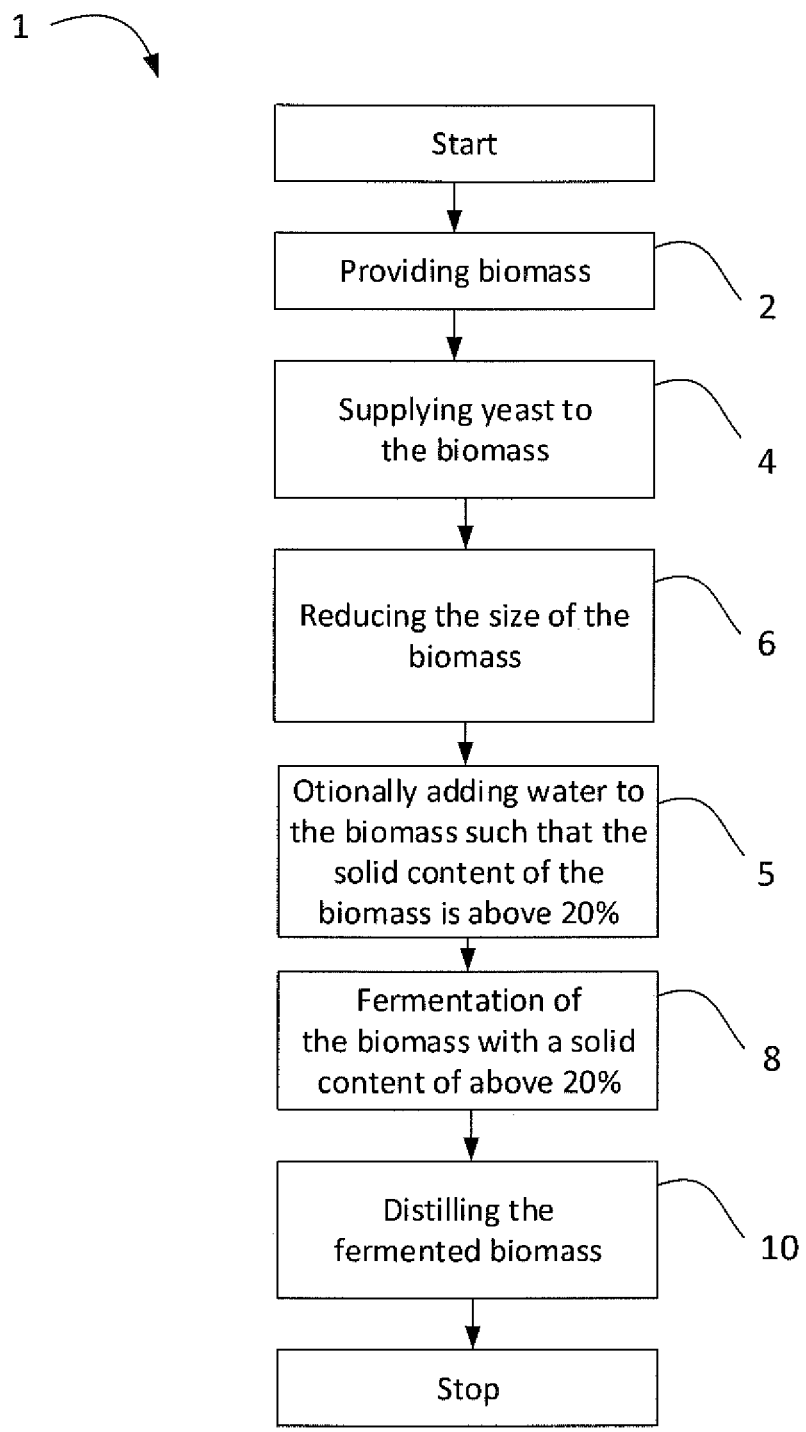
FIG. 1 shows a flow diagram illustrating the steps of an embodiment of method for producing ethanol according to the first aspect of the invention.

FIG. 1 shows a flow diagram illustrating the steps of the method for producing ethanol 1 according to an embodiment of the present invention. The method for producing ethanol 1 will be described together with FIG. 1 and also together with FIG. 3 which shows an ethanol producing system 100 according to an embodiment of to the present invention. The method for producing ethanol 1 comprises the steps of providing 2 biomass, supplying yeast 4 to the biomass 4, reducing the size 6 of the biomass, fermentation 8 of the biomass with a solid content of above 20% and distilling 10 the fermented biomass. In other embodiments, the method comprises adding water to the biomass such that the solid content of the biomass is above 20%.

For the purposes of the present application, the term "biomass" refers to cellulosic or lignocellulosic biomass derived from plants, and includes material comprising cellulose, hemicellulose, lignin, starch, oligosaccharides and/or monosaccharides. The biomass may be derived from one sole source or may comprise a mixture derived from more than one source. For example, a biomass may comprise a mixture of material of different plant species. Biomass includes, without being limited to bioenergy crops, agricultural and forestry residues. Examples of biomass include, but are not limited to plant material derived from a plant selected from among the group consisting of sugar cane, energy cane, corn, soybean, sorghum, millet rye, wheat, triticale, oat, barley, rice, alfalfa. Napier grass, *Miscanthus*, cotton, agave, hemp, jute, *eucalyptus*, pine, willow, tobacco, clover, bamboo, linen, sweet potato, potato, manioc, yarn, beetroot and canolla. Preferably, the biomass comprises sugar cane and/or energy cane and/or sorghum. Sorghum doesn't require ideal growing conditions and is thus relatively inexpensive to grow. Thereby it is possible, if sorghum is used as raw material, to provide a method 1 for producing ethanol which is less expensive.

At first raw biomass is provided 2 by growing the biomass on a field or several fields, harvesting the biomass from the field(s) and transporting the biomass. The biomass is harvested in forage form, i.e. the length of the biomass is reduced to a length less than about 100 mm during harvesting, for example by chopping and/or shredding the plants of biomass. Preferably, whole plants of biomass are used. Thus, all parts of a biomass plant, i.e. stalk, leaves and seed stalk, is used. Thereby, the yield of ethanol per acre of cultivated field is increased and the disposal of residual solids is reduced.

Optionally, the biomass may be subjected to cleaning 22 for removal of plant or mineral impurities that might be present in the biomass material. This operation improves the quality of the raw material that will be further processed and it extends the life time of the ethanol producing system 100, as it reduces the damage related to abrasion due to the presence of, for example, sand and stones, particularly upon biomass having been mechanically harvested. The cleaning 22 of the biomass may be conducted by means of for example filtration, decanting, flotation, sedimentation, grinding, washing followed by filtration, sieving and dry cleaning.

Afterwards yeast is supplied 4 to the biomass (either or not cleaned). The yeast is in a liquid and/or a solid form. It is possible to use any kind of yeast that can ferment glucose into ethanol. Thereafter, the biomass with the added yeast is conveyed 24, preferably by means of a screw conveyor, which is an apparatus that uses a rotating helical screw blade within a tube to move the biomass with added yeast, to the biomass size reducing device 106 to reduce the size 6 of the biomass. Thus, the step of supplying yeast 4 to the biomass is performed before the step of reducing the size 6 of the biomass. Thereby the mixing of the biomass and the added yeast is improved. It is also possible to supply yeast 4 directly to the conveying device 124. In that way the step of supplying yeast 4 will be performed simultaneously as the step of conveying 24 the biomass. This also improves the mixing of the biomass and the added yeast.

Optionally, water is added 5 to the biomass such that the solid content of the biomass is above 20%, or preferably above 50% and most preferably above 80%. The solid content of the biomass is the mass of solids remaining after a sample of biomass has been dried in an oven at about 103-105° C. for about 24 hours, divided by the original mass of the sample. Preferably however, no water is used before the step of fermentation 8 of the biomass.

The size of the biomass is reduced 6 by reducing the length of the biomass to a length in the range between about 1-2 mm preferably, the size of the biomass is reduced 6 by means of an atmospheric refiner. An atmospheric refiner is an equipment operated under atmospheric pressure for refining, for example rubbing or grinding, the biomass material into fibres and/or particles. The atmospheric refiner comprises two refiner plates and the biomass is fed between the plates. The refining energy used by the atmospheric refiner is preferably in the range of about 100-300 kWhr/bdt (kilowatt hour/bone dry ton) of biomass fibre. An atmospheric refiner only processes the biomass mechanically and do not degrade the free sugar molecules in the biomass. Thus, no water or chemicals are used during the step of reducing the size 6 of the biomass. Thereby, no evaporation is needed.

Thereafter, the biomass is fermented 8, preferably by means of a fermentation downward tower which is a down flow reactor with agitation only at the bottom of the fermentation downward tower where the biomass material is discharged from the fermentation downward tower. During fermentation 8 of the biomass, the free sugar molecules of the biomass are fermented into ethanol. After fermentation 8, the water content by mass in the biomass has increased from about 70% to about 80% because the free sugar and starch has been converted into ethanol and $CO_2$. After that the fermented biomass is finally distilled 10, preferably by means of a distillation column, to purify and concentrate the produced ethanol.

Figure 2:
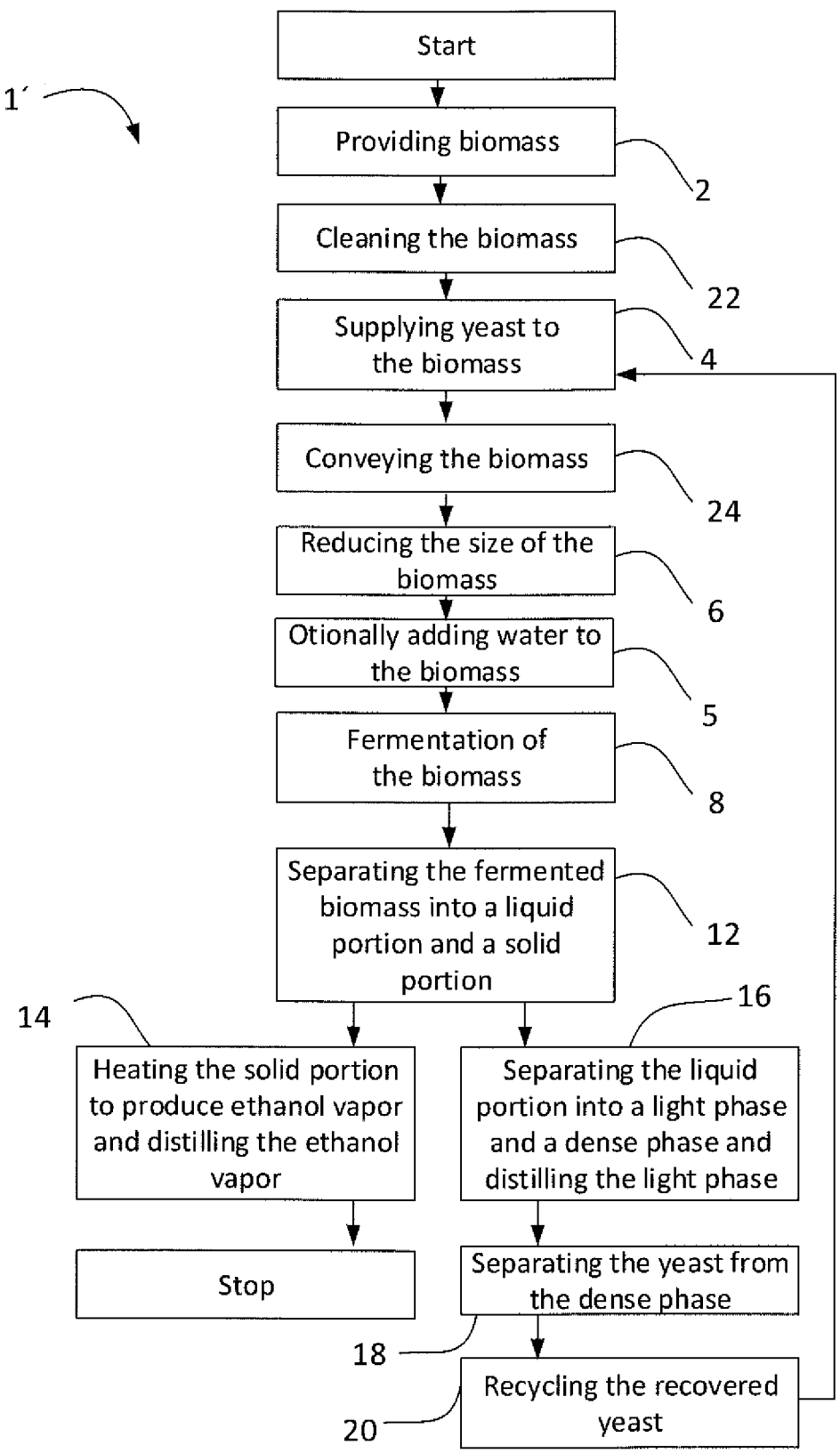
FIG. 2 shows a flow diagram illustrating the steps of another embodiment of a method for producing ethanol according to the first aspect of the invention.

FIG. 2 shows a flow diagram illustrating the steps of a method for producing ethanol 1' according to another embodiment of the present invention. The method 1' will be described together with FIG. 2 and also together with FIG. 4 which shows an ethanol producing system 100' according to another embodiment of to the present invention. FIG. 2 is exactly the same as FIG. 1 except from that the method for producing ethanol 1' shown in FIG. 2 comprises additional steps. Thus, the above text describing the steps of providing 2 biomass, supplying yeast 4 to the biomass, optionally adding water 5 to the biomass in such a manner that its solid content is above 20%, reducing the size 6 of the biomass, fermentation 8 of the biomass at a solid content of above 20%, and distilling 10 the fermented biomass is also true for the method for producing ethanol 1' according to the below described other embodiment of the present invention. The additional steps comprised in the method for producing ethanol 1' according to the other embodiment of the present invention is described below.

After the biomass has been fermented 8, the biomass is separated 12, preferably by means of a screw press, into a liquid portion and a solid portion such that the water content of the solid portion is about 45%. The screw press is a dewatering screw press that accomplishes dewatering by continuous gravitational drainage. The screw press squeezes the biomass material against a screen and/or filter and the liquid is collected through the screen and/or filter.

Thereafter, the solid portion is heated 14, preferably by means of a horizontal screw reactor, to 100° C. to vaporize left over ethanol in the solid portion. A screw reactor is a continuous reactor where the solid portion, in addition to be heated, is transported and mixed by a screw. Thereafter the ethanol vapour is distilled, preferably by means of a distillation column. The residual bagasse, i.e. the residual solid material, can be further processed, for example dewatered and hydrolysed.

The liquid portion is separated 16, preferably by sedimentation which is a physical liquid treatment process using gravity to remove suspended solids from the liquid, into a light phase and a dense phase. The light phase is distilled, preferably by means of a distillation column. After that, the yeast is separated 18, preferably by centrifuging which separates substances of different densities by centrifugal force, from the dense phase. It is also possible to separate the yeast 18 by means of cross flow membrane separation where the dense phase is passed across a filter membrane tangentially. After that the yeast is recycled 20 by using the recovered yeast in the step supplying yeast 4 to the biomass.

Figure 3:
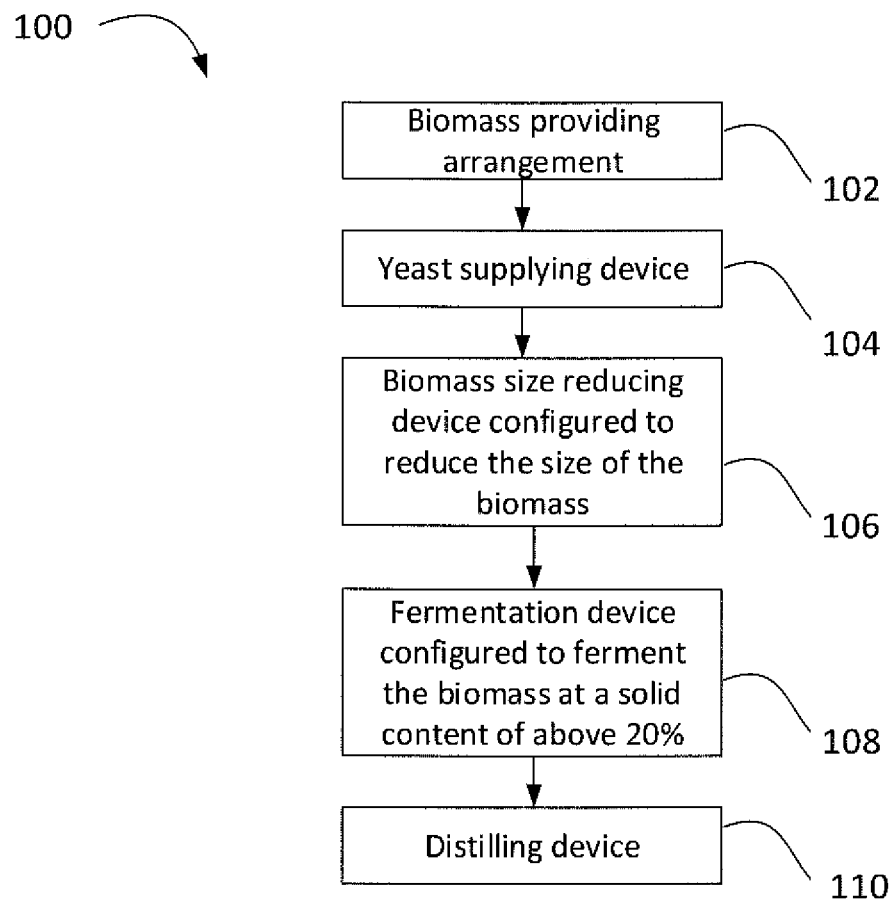
FIG. 3 shows schematically an embodiment of an ethanol producing system according to the second aspect of the invention.

FIG. 3 shows an ethanol producing system 100 according to an embodiment of the present invention. The arrows in FIG. 3 illustrates the flow of biomass. The ethanol producing system 100, comprises a biomass providing arrangement 102, a yeast supplying device 104 for supplying yeast to the biomass, a biomass size reducing device 106 configured to reduce the size of the biomass, a fermentation device 108 configured for fermentation of the biomass at a solid content of above 20%, and a distilling device 110. Thereby, it is possible to provide an ethanol producing system 100 which is less complicated, do not require chemicals, is more environmentally friendly and less expensive. In other embodiments, the system comprises a water addition device for adding water to the biomass, either before or after the biomass size reducing device 106.

The biomass providing arrangement 102 comprises a growing arrangement, harvesting arrangement and a transporting arrangement for transporting the biomass to the yeast supplying device 104. The growing arrangement comprises for example a planting device for planting biomass and a water supply device for supplying water to the plants. The biomass is grown on a field or several fields. The harvesting arrangement harvests the biomass from the field(s) in forage form, i.e. the harvesting arrangement reduces the length of the biomass to a length less than about 100 mm by chopping and/or shredding the plants of biomass. Preferably, the harvesting arrangement harvests whole plants of biomass. Thus, all parts of a biomass plant, i.e. stalk, leaves and seed stalk, are harvested. The transporting arrangement can for example comprise a truck.

Optionally, the ethanol producing system 100 comprises a cleaning device 122 for cleaning 22 the biomass to remove plant or mineral impurities that might be present in the biomass material. This operation improves the quality of the raw material that will be further processed and it extends the life time of the ethanol producing system 100, as it reduces the damage related to abrasion due to the presence of, for example, sand and stones, particularly upon biomass having been mechanically harvested. The cleaning device 122 can for example comprise a filtration device, a decanting device, a flotation device, a sedimentation device, a grinding device, a washing device, a sieving device or a dry cleaning device.

Afterwards the yeast supplying device 104 supplies yeast to the biomass (either cleaned or not). The yeast is in a liquid and/or a solid form. It is possible to use any kind of yeast that can ferment glucose into ethanol. Thereafter, a conveying device 124 conveys the biomass with the added yeast from the yeast supplying device 104 to the biomass size reducing device 106. Thus, the yeast supplying device 104 is arranged upstream the biomass size reducing device 106. Thereby, the biomass and the yeast are mixed in the biomass size reducing device 106 and thereby the mixing of the biomass and the yeast is improved. Preferably, the conveying device 124 comprises a screw conveyor. If that is the case, the yeast supplying device 104 is arranged upstream the screw conveyor. Thus, the yeast supplying device 104 supplies yeast to the biomass before the size reducing device 106 reduces the size of the biomass. It is also possible for the yeast supplying device 104 to supply yeast directly to the biomass in the conveying device 124, i.e. the yeast is supplied 4 to the biomass and the biomass is conveyed 24 simultaneously.

The biomass size reducing device 106 reduces the size of the biomass, and is configured to reduce the length of the biomass to a length in the range between 1-2 mm. Thereby the surface area of the biomass material is increased and thereby it is possible to provide an ethanol producing system 100 which produces a higher yield of ethanol per unit weight of total solids in the raw material. Preferably, the size reducing device 106 comprises an atmospheric refiner. The refining energy used by the atmospheric refiner is preferably in the range of 100-300 kWhr/bdt (kilowatt hour/bone dry ton) of biomass fibre.

Thereafter, the biomass is fermented 8 by means of the fermentation device 108. Preferably, the fermentation device 108 comprises a fermentation downward tower. During fermentation 8 of the biomass, the free sugar molecules of the biomass are fermented into ethanol. After fermentation 8, the water content by mass in the biomass has increased from about 70% to about 80% because the free sugar and starch has been converted into ethanol and $CO_2$. After that the fermented biomass is finally distilled 10 by means of the distillation means 110, preferably by means of a distillation column, to purify and concentrate the produced ethanol.

Figure 4:
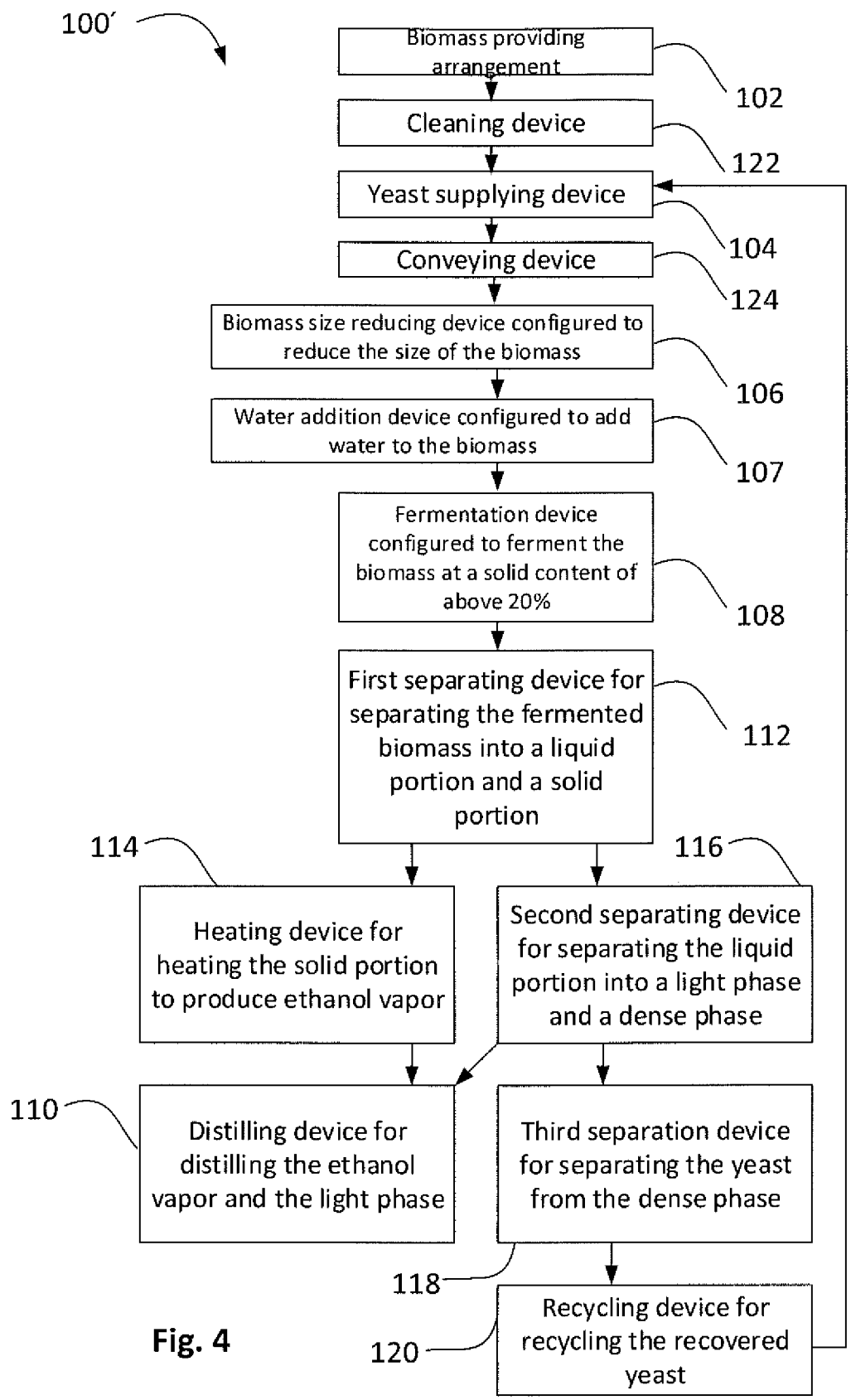
FIG. 4 shows schematically an embodiment of an ethanol producing system according to the second aspect of the invention.
Figure 5:
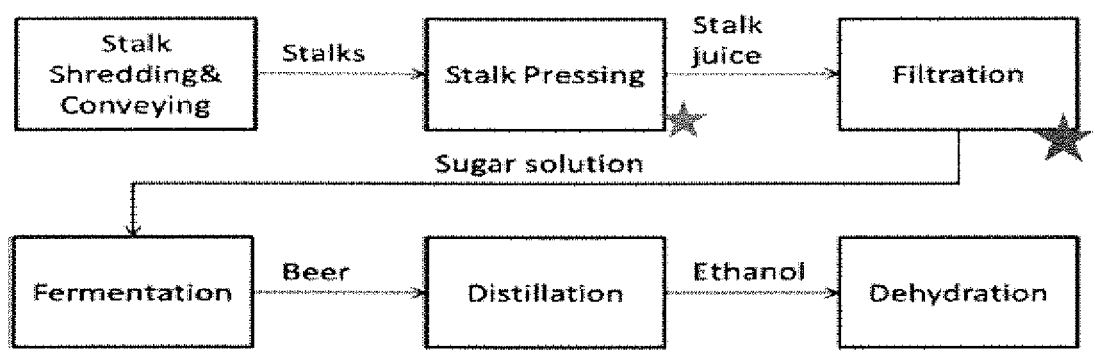
FIG. 5 shows an ethanol producing system according to the prior art.

FIG. 4 shows an ethanol producing system 100' according to an embodiment of the present invention. FIG. 4 is exactly the same as FIG. 3 except from that the ethanol producing system 100' in FIG. 4 comprises additional means. Thus, the above text describing the biomass providing arrangement 102, the yeast supplying device 104, the biomass size reducing device 106, the fermentation device 108 and the distilling device 110 is also true for the ethanol producing system 100' according to the below described other embodiment of the present invention. The additional means comprised in the ethanol producing system 100' according to the other embodiment of the present invention is described below. The arrows in FIG. 4 illustrates the flow of biomass.

After the biomass has been fermented 8 the biomass is separated 12 by means of first separating device 112, which preferably comprises a screw press, into a liquid portion and a solid portion such that the water content of the solid portion is about 45%.

Thereafter, the solid portion is heated 14 by means of heating device 114, which preferably comprises a horizontal screw reactor, to 100° C. to vaporize left over ethanol in the solid portion. The residual bagasse, i.e. the residual solid material, can be further processed, for example dewatered by means of dewatering means (not shown) and hydrolysed by hydrolysing means (not shown).

Thereafter the ethanol vapour is distilled by means of distillation device 110. Preferably the distillation device 110 comprises a distillation column. The liquid portion is separated 16 by means of second separating device 116 into a light phase and a dense phase. Preferably, the second separating device 116 comprises a sedimentation device. Thereafter the light phase is distilled by means of distillation device 110. Preferably, the distillation device 110 comprises a distillation column. After that, the yeast is separated from the dense phase 18 by means of the third separation device 118. Preferably, the third separation device 118 comprises a centrifuge. It is also possible to separate the yeast by means of cross flow membrane separation where the dense phase is passed across a filter membrane (not shown) tangentially. After that the yeast is recycled 20 by a recycling device 120 which recycles the recovered yeast to the yeast supplying device 104.

The present invention is of course not in any way restricted to the preferred embodiments described above, but many possibilities to modifications, or combinations of the described embodiments, thereof should be apparent to a person with ordinary skill in the art without departing from the basic idea of the invention as defined in the appended claims.

The invention claimed is:
1. A method for producing ethanol, comprising:
providing biomass,
supplying yeast to the biomass,
refining the biomass to reduce its size,
optionally adding water to the biomass such that the solid content of the biomass is above 20% by weight,
fermentation of the biomass with a solid content of above 20% by weight, and
distilling the fermented biomass,
wherein the step of supplying yeast to the biomass is performed before the step of refining the biomass to reduce its size.

2. The method according to claim 1, wherein no water is added before the step of fermentation of the biomass.

3. The method according to claim 1, wherein refining the biomass to reduce its size comprises using an atmospheric refiner.

4. The method according to claim 1, wherein providing biomass comprises providing whole plants.

5. The method according to claim 1, further comprising: separating the fermented biomass into a liquid portion and a solid portion.

6. The method according to claim 5, further comprising: heating the solid portion to produce ethanol vapour, and distilling the ethanol vapour.

7. The method according to claim 5, further comprising: separating the liquid portion into a light phase and a dense phase, and
distilling the light phase.

8. The method according to claim 7, wherein separating the liquid portion comprises sedimentation of the liquid portion.

9. The method according to claim 8, further comprising: separating the yeast from the dense phase to provide recovered yeast.

10. The method according to claim 9, wherein separating the yeast comprises centrifuging the dense phase.

11. The method according to claim 9, further comprising: recycling the yeast by using the recovered yeast in the step comprising supplying yeast to the biomass.

12. The method according to claim 1, wherein providing biomass comprises providing sugar cane and/or energy cane and/or sorghum.

13. The method according to claim 1, wherein providing biomass comprises growing the biomass, harvesting the biomass and transporting the biomass.

14. The method according to claim 13, wherein harvesting the biomass comprises reducing the length of the biomass to a length less than 100 mm.

15. The method according to claim 1, wherein refining the biomass to reduce its size comprises reducing the length of the biomass to a length in the range between 1-2 mm.

16. The method according to claim 1, wherein the fermentation comprises using a fermentation downward tower.

17. The method according to claim 5, wherein separating the fermented biomass comprises using a screw press.

18. The method according to claim 6, wherein heating the solid portion comprises using a horizontal screw reactor.

19. The method according to claim 1, wherein distilling comprises using a distillation column.

20. The method according to claim 1, further comprising conveying the biomass using a screw conveyer, and supplying yeast to the biomass comprises supplying yeast to the biomass in the screw conveyor.

21. The method according claim 1, wherein cleaning the biomass is performed before the step of supplying yeast to the biomass.

22. The method according to claim 1, wherein the solid content of the biomass is above 50%.

23. The method according to claim 1, wherein the solid content of the biomass is above 80%.

* * * * *